US009629542B2

(12) United States Patent
Engelhardt et al.

(10) Patent No.: US 9,629,542 B2
(45) Date of Patent: Apr. 25, 2017

(54) METHOD AND DEVICE FOR THE SEQUENTIAL RECORDING OF INTERFEROMETRIC DEEP SECTIONAL IMAGES AT DIFFERENT DEPTHS, IN PARTICULAR FOR ANALYSIS OF THE EYE

(75) Inventors: Ralf Engelhardt, Luebeck (DE); Gerit Droege, Luebeck (DE); Bjoern Martensen, Luebeck (DE)

(73) Assignee: Heidelberg Engineering GmbH, Heidelberg (DE)

( * ) Notice: Subject to any disclaimer, the term of this patent is extended or adjusted under 35 U.S.C. 154(b) by 23 days.

(21) Appl. No.: 13/981,667

(22) PCT Filed: Feb. 3, 2012

(86) PCT No.: PCT/EP2012/000487
§ 371 (c)(1),
(2), (4) Date: Jul. 25, 2013

(87) PCT Pub. No.: WO2012/104097
PCT Pub. Date: Aug. 9, 2012

(65) Prior Publication Data
US 2013/0308096 A1 Nov. 21, 2013

(30) Foreign Application Priority Data
Feb. 4, 2011 (DE) .......................... 10 2011 010 443

(51) Int. Cl.
*A61B 3/14* (2006.01)
*A61B 3/10* (2006.01)
*G01B 9/02* (2006.01)

(52) U.S. Cl.
CPC .......... *A61B 3/102* (2013.01); *G01B 9/02064* (2013.01); *G01B 9/02085* (2013.01); *G01B 9/02091* (2013.01); *G01B 2290/35* (2013.01)

(58) Field of Classification Search
CPC ......... A61B 3/0025; A61B 3/102; A61B 3/14; A61B 3/12; A61B 3/113; A61B 3/0008;
(Continued)

(56) References Cited

U.S. PATENT DOCUMENTS 5,170,276 A   12/1992 Zinser
2004/0154402 A1* 8/2004 Drake, Jr. ....................... 73/621
(Continued)

FOREIGN PATENT DOCUMENTS

DE          41 03 298      8/1992
WO     WO-2008/052793     5/2008
(Continued)

*Primary Examiner* — Scott J Sugarman
*Assistant Examiner* — Sharrief Broome
(74) *Attorney, Agent, or Firm* — Norris McLaughlin & Marcus, P.A.

(57) ABSTRACT

A method and apparatus including an interferometer is provided for sequentially recording interferometric sectional images at different depths, in particular for analyzing an eye. By use of an interferometer, which includes an optical reference path and an optical sample path, a sample beam scans a measuring region of a sample, in particular of an eye, so as to generate a deep sectional image. The optical and geometric paths in a sample arm and/or reference arm of the interferometer can be switched quickly between two or more positions. The path length of the sample beam and/or of the reference beam is changed by way of a path length switching unit, deep sectional images are generated at least at two different depths of the sample, and the change of the path length in the switching unit takes place by deflection of the beam paths to different geometric paths.

22 Claims, 6 Drawing Sheets

(58) Field of Classification Search
CPC ......... A61B 3/1015; A61B 3/103; A61B 3/10;
A61B 3/1025; A61B 3/117; A61B 3/13;
A61B 3/0041; A61B 3/0058; A61B
3/1005; A61B 3/18; A61B 3/032; A61B
3/1225
USPC ....... 351/200, 205, 206, 210, 221, 246, 209,
351/222
See application file for complete search history.

(56) References Cited

U.S. PATENT DOCUMENTS

| | | | |
|---|---|---|---|
| 2005/0225743 A1* | 10/2005 | Chang | G01C 3/08 |
| | | | 356/5.01 |
| 2007/0058173 A1* | 3/2007 | Holzapfel | H05G 2/008 |
| | | | 356/499 |
| 2010/0053553 A1 | 3/2010 | Zinser | |
| 2010/0283970 A1* | 11/2010 | Sekiguchi | A61B 3/12 |
| | | | 351/206 |
| 2011/0234975 A1 | 9/2011 | Hirose | |

FOREIGN PATENT DOCUMENTS

| | | | | |
|---|---|---|---|---|
| WO | WO-2010/074098 | | 7/2010 | |
| WO | WO 2010074098 A1 * | | 7/2010 | ............... G01B 9/02 |

* cited by examiner

METHOD AND DEVICE FOR THE SEQUENTIAL RECORDING OF INTERFEROMETRIC DEEP SECTIONAL IMAGES AT DIFFERENT DEPTHS, IN PARTICULAR FOR ANALYSIS OF THE EYE

BACKGROUND OF THE INVENTION

The invention relates to a method for sequentially recording interferometric deep sectional images. The invention further relates to a device for carrying out the method.

The recording of interferometric deep sectional images is associated with the problem that the device only allows a limited measuring depth for a particular reference arm length. In Fourier domain systems, the measuring depth is limited by the resolution of the spectral apparatus. Rapidly operating systems typically detect depths with a distance of up to 10 mm from the reference plane with acceptable signal-to-noise ratio.

In addition, the depth of field of the optical system that is employed often limits the measuring depths when recording interferometric deep sectional images. Typically, only ranges in the order of magnitude of the Rayleigh length can be recorded with good lateral resolution and acceptable signal-to-noise ratio. An expansion of the measuring depth to several times the Rayleigh length often requires the focal position to be adjusted.

One of the factors that the depth resolution of interferometric deep sectional images depends on is the adaptation of the dispersion in the arms of the interferometer that is employed. The dispersion of conventional systems is only adapted to one measuring depth, so that expanding the measuring depth generally entails a loss of axial resolution.

According to the invention, these problems listed here are to be solved for rapidly operating interferometric imaging systems.

So as to adjust the region of a sample that is scanned with a good signal-to-noise ratio to a new depth, the path length difference between the sample path and the reference path, and optionally the imaging geometry and the focus position, as well as the dispersion, must be changed. In particular in the case of movable samples (for example when measuring the eye), the change of the path length difference and, if required, the change of the focus position, and optionally the change of the dispersion adaptation, must take place quickly, so as to obtain information about the relative positions of the scanned regions with respect to each other, and optionally be able to assemble a complete deep sectional image from several sequentially recorded individual deep sectional images. Modern interferometric measuring systems achieve frame rates of several 100 Hz. A controlled change of the position of the measuring apparatus relative to the sample or the position of the mirror in the reference arm is not possible when switching to differing regions within a time of considerably less than 10 ms (for example 1 ms for a maximum of 10% dead time at a frame rate of 100 Hz), because here paths of several mm must be covered.

SUMMARY OF THE INVENTION

It is the object of the invention to propose a method and a device, by way of which the optical and geometric paths in a sample arm and/or reference arm of an interferometer can be switched quickly between two or more positions. The option is to be created for interferometric deep sectional images at different depths to be generated and/or recorded at an improved signal-to-noise ratio in the respective scanned region. Additionally, it is to be made possible to generate a deep sectional image having an expanded measuring depth in a simple manner. The method should be easy to carry out in a functionally reliable manner and supply reliable and/or improved results with low expenditure.

In addition, the method and the device are to provide the option of adapting, either in individual or all positions, the focus position or the imaging geometry and/or the dispersion adaptation to the respective position.

The invention provides a method and a device for a switching unit so as to switch the optical paths in the sample arm and/or reference arm of an interferometer very quickly between two or more positions. The switching unit is preferably located in the sample arm because this allows a closed design for the reference arm, for example in a fiber interferometer. However, in principle, the switch can be in both arms, with limitations in terms of the functionality. The switching unit can also be used to modify additional parameters such as the position of the focus, imaging geometry and dispersion, by introducing elements into the switched paths. The quick switching allows the measuring region to be shifted to different depths with minimal dead time. The invention is implemented in particular by way of a Michelson interferometer, however other interferometers, such as Mach-Zehnder systems, can also be provided within the scope of the invention.

According to the invention, the path length switching unit is preferably implemented with movable mirrors. This allows the required fast switching times to be achieved, and the option exists to conduct the beam paths for the different positions on different optical paths and through different optical elements. A mirror mounted on a galvanometer motor can be adjusted to a new position within 0.1 ms according to the related art.

Special refinements and embodiments are provided in the dependent claims and the description of exemplary embodiments shown in the drawings. The invention will be described in greater detail hereafter based on the special exemplary embodiments shown in the drawings, without thereby limiting the invention in this respect. In the representative illustrations are shown:

Figure 1:
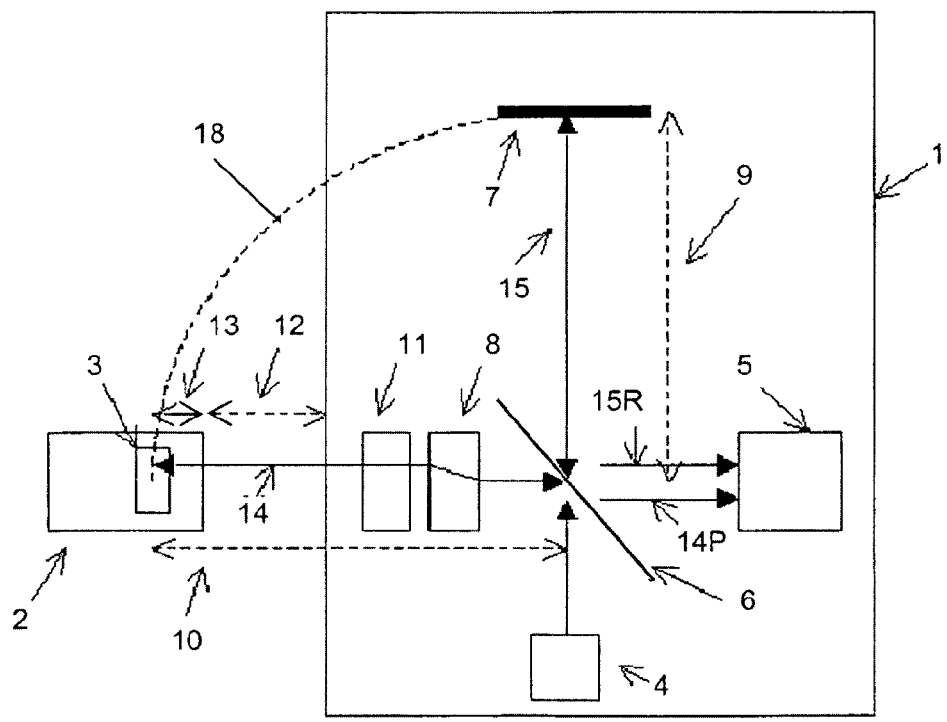
FIGS. 1 to 3 show a typical interferometric measuring arrangement.

FIG. 1 shows a typical interferometric measuring arrangement for recording deep sectional images, here based on a Michelson interferometer. A deep sectional image is recorded in a region 3 within the sample 2 by the measuring apparatus 1 designed as an interferometer. The light from the light source 4 is incident on the beam splitter 6 and is split into the sample beam 14 and the reference beam 15. The arrows at the respective ends of the sample beam 14 and reference beam 15 denote the directions of the illumination beams emitted by the light source 4 and also the reflected or re-emitted corresponding light beams. The deep sectional image is computed in the evaluation unit 5 by evaluation of the interferometric signals, which result due to superimposition of the sample beam 14P and reference beam 15R at various lateral positions on the sample. So as to generate deep sectional images, the sample beam 14 is deflected by the deflecting unit 8 at various lateral positions of the sample 2. The optional optical unit 11 focuses the sample beam 14, if necessary, at a predetermined depth of the object or of the sample and/or of the measuring region. The deep sectional image is recorded at the depth 13 of the sample, at which the optical reference path 9 and the optical sample path 10 are identical, as indicated by the dotted line 18. The depth is defined both by the position of the mirror 7 and by the distance 12 of the measuring apparatus 1 from the sample 2.

Figure 2:
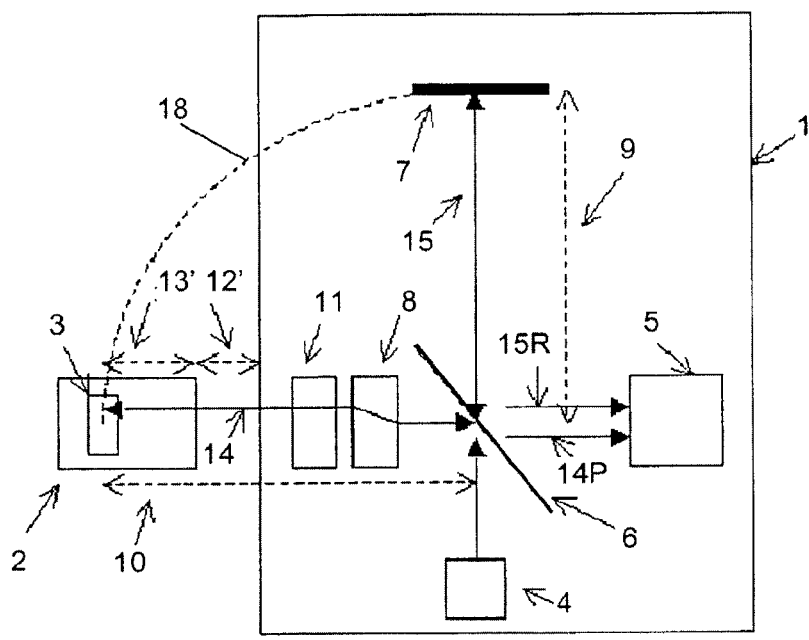
Figure 3:
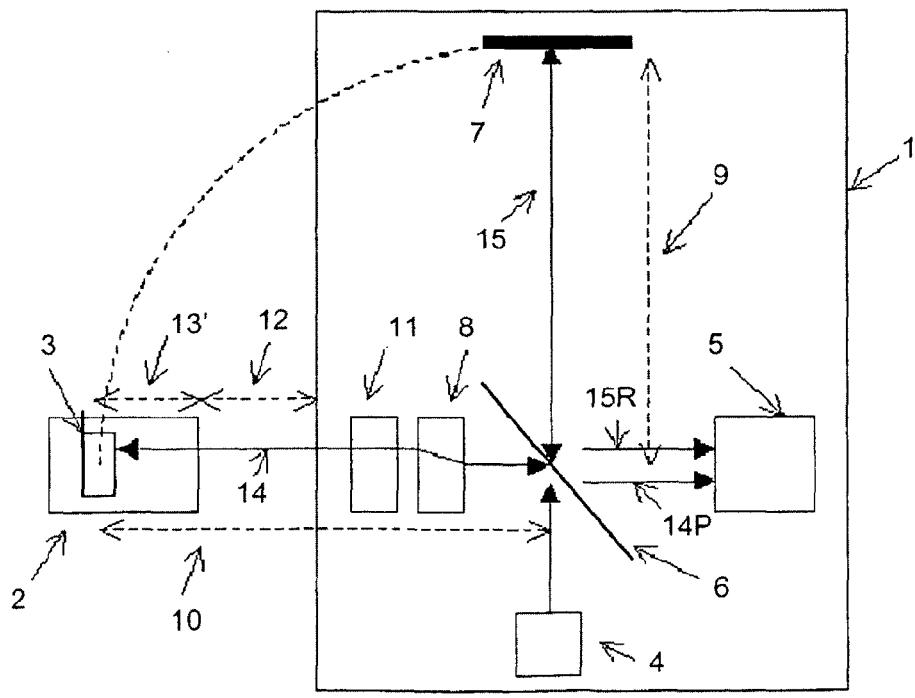

If the measuring region 3 is to be adjusted to a new depth 13 for the deep sectional image, the distance between the measuring apparatus 1 and the sample 2 can be changed, as shown in FIG. 2. By changing the distance 12', the measuring region here is placed at the new depth 13'. The same result can be achieved by changing the optical path 9 of the reference beam 15, while maintaining the distance 12, as shown in FIG. 3. Again, the measuring region 3 is shifted to the new depth 13'.

By sequentially recording at least two deep sectional images at different depths, according to the invention a complete deep sectional image having an expanded measuring depth is generated by assembling the individual images.

Figure 4:
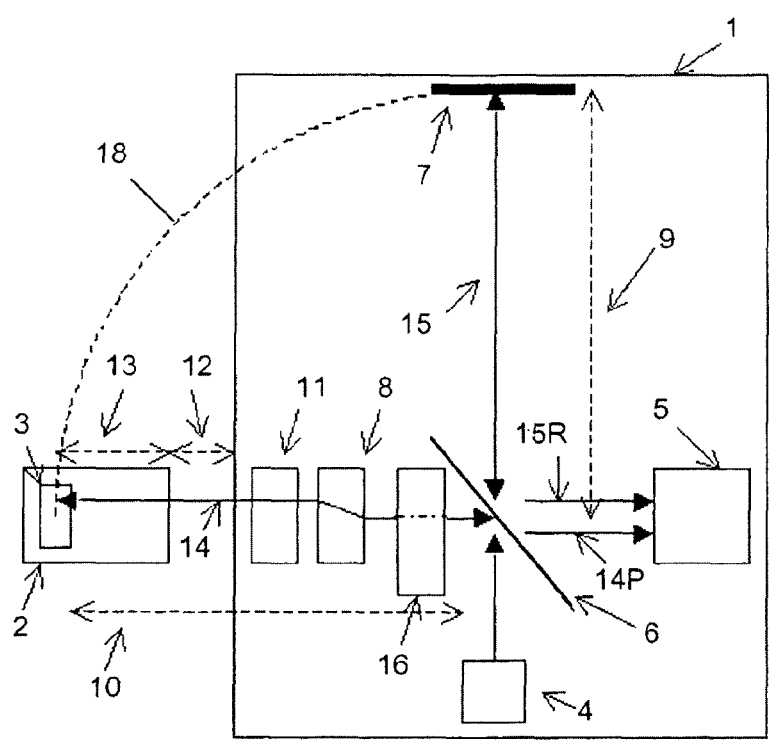
FIGS. 4, 5 show an exemplary embodiment of the interferometric measuring arrangement according to the invention comprising a path length switching unit.

FIG. 4 shows the principle using the example of a path length switching unit 16 that is inserted according to the invention into the sample path 14, wherein the position of the measuring region 3 at the depth 13 is located at the depth 13 within the sample 3 in the case of a short optical path in the path length switching unit. According to FIG. 5, the optical path length has been switched to a longer optical path in the path length switching unit, as indicated by the dotted line 17, which is extended as compared to FIG. 4. With all other variables remaining unchanged, a measuring region at a new, lesser depth 13" within the sample 2 is now scanned. Depending on the configuration of the path length switching unit 16, it is possible according to the invention to implement two or more measuring region positions. According to the invention, the focus of the optical unit 11 is adapted to the optical path length set by way of the path length switching unit 16 and/or to the set position of the measuring region 3.

Figure 5:
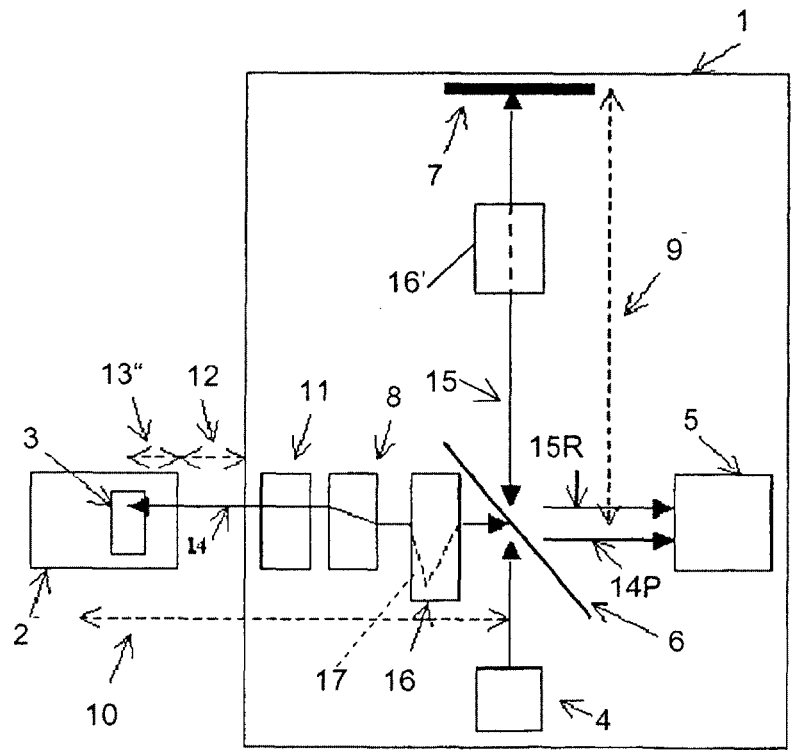

FIG. 5 shows an additional or alternative embodiment, which includes the path length switching unit 16' in the reference path or reference beam 15. Analogous to the path length switching unit 16 in the sample path or sample beam 14, this path length switching unit 16' can used to change and/or set the path length in the reference path or reference beam 15.

Figure 6:
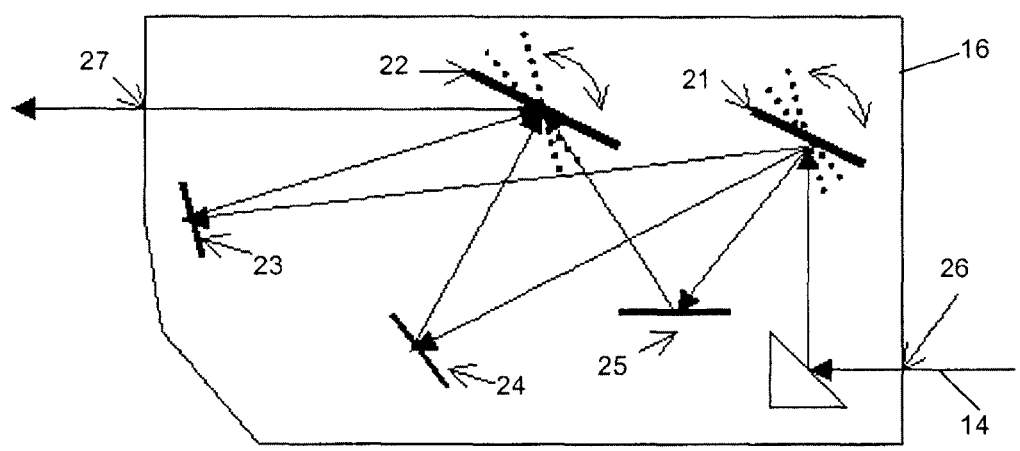
FIG. 6 is a special embodiment of the path length switching unit.

FIG. 6 shows a special embodiment of the path length switching unit 16. Depending on the mirror position, the light beam 14 incident at position 26 is deflected to one of the mirrors 23, 24 or 25 by way of the rotatable mirror 21. The mirrors 23, 24 and 25 are oriented in each case such that the light beam incident from the mirror 21 is deflected to the axis of the rotatable mirror 22. The angle and/or the angular position of the mirror 21 and/or 22 is adjusted suitably for, and/or preferably synchronously with, the respective paths, by way of the mirror 23 or 24 or 25, so that the beam always exits the path length switching unit 16 at position 27. The positions of the mirrors 23, 24 and 25 are selected in this embodiment so that the mirror 21/mirror 23/mirror 22 segment, the mirror 21/mirror 24/mirror 22 segment, and the mirror 21/mirror 25/mirror 22 segment are different from each other, and more particularly by magnitudes that correspond to the desired shifts of the measuring region. Motors are associated with the mirrors 21, 22, the motors allowing fast adjustment of the mirrors 21, 22; in particular, these motors are galvanometers. The three different combinations for the mirror angles 21 and 22 thus allow three different path lengths between positions 26 and 27 to be switched very quickly. The principle is not limited to three paths and, depending on the embodiment of the path length switching unit 16, two or more paths can be implemented. Of course, the reflected or remitted light beam conversely enters the path length switching unit 16 at position 27 and exits at position 27.

Depending on the properties of the sample and the measuring task, it may be necessary to adapt the position of the focus and/or the dispersion to the respective depth of the measuring region. According to the invention, a different focus position is defined for each of the settable measuring regions by introducing optical components into the different paths of the path length switching unit, in particular when considering the optical unit 11 according to FIG. 1 to FIG. 5. In addition, the dispersion in the different paths of the path length switching unit can be set differently and/or adapted to the depth of the measuring region by selecting the dispersion of the optical components.

Figure 7:
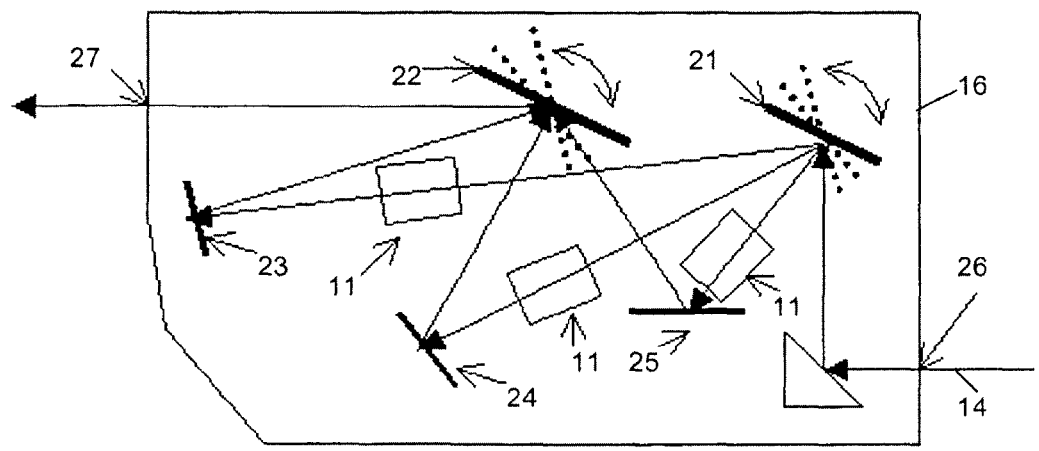
FIG. 7 shows the path length switching unit of FIG. 6 with integrated optical components.

FIG. 7 shows a possible arrangement of the components 8, 9 and 10 described based on FIG. 1 to FIG. 5 in the arrangement shown in FIG. 6.

In a further special embodiment, the path length switching unit according to FIG. 6 or FIG. 7 is combined with the optical unit 11 of FIG. 1 to FIG. 5 because, in general, the optical unit 11 likewise includes rotatable mirrors for beam deflection and the direction of the sample beam can preferably be changed by way of the mirror 22 of FIG. 6 or FIG. 7.

The method is not limited to recording deep sectional images. The fast switching of the path lengths and/or of the focus position and/or of the dispersion can likewise be utilized for one-dimensional measurements along an axis.

It shall be pointed out here that the deep sectional images are captured in the known manner by way of scanning or sampling in lines and columns and/or are generated by way of the evaluation unit. In a special alternative embodiment of the invention, only a single column, or optionally just a few columns, and more particularly a maximum of 10 columns, are generated at a depth, instead of a complete deep sectional image. The duration of the method and/or the measuring time can thus be reduced quite significantly.

Volume images can be generated by recording deep sectional images at different lateral positions. The measuring region can also be expanded here by use of the path length switching unit.

Interferometric measuring techniques for recording deep sectional images have attained great significance in medical diagnostics. Here, these measuring techniques are known by the term "OCT" (optical coherence tomography). Deep sectional images can be generated at great depths especially in ophthalmology, and a large measuring region is required.

Figure 8:
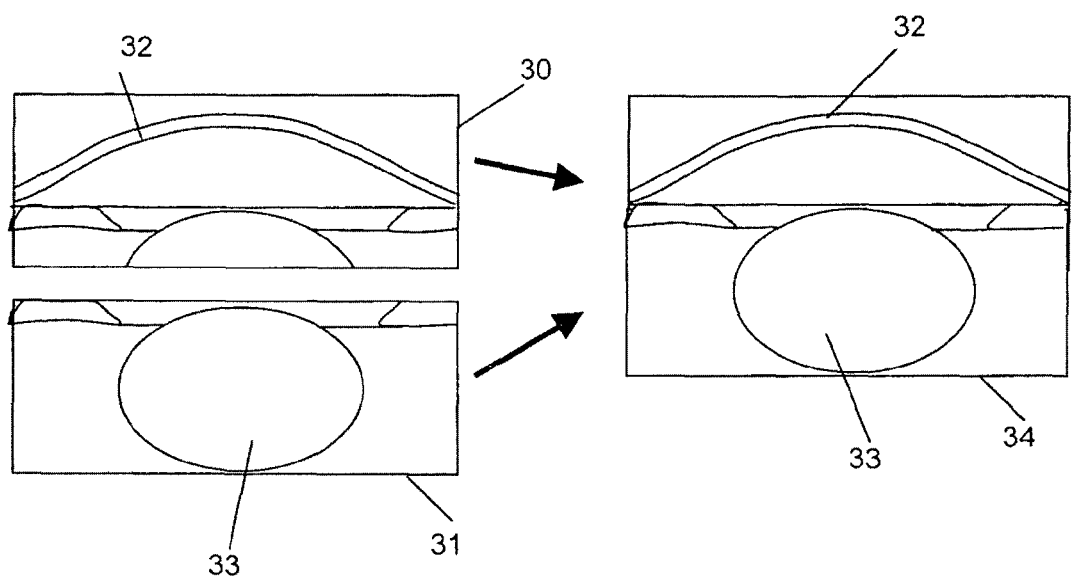
FIG. 8 shows the assembly of individual deep sectional images at different depths to form a complete deep sectional image.

On the left, FIG. 8 is a schematic illustration of deep sectional images 30, 31 that were recorded using a measuring region of 8 mm, in each case at different depths of the human eye, and using different focal positions, which are suited to the different depths. These images were recorded with a path length switching unit having two paths. Deep sectional images can be generated over the entire depth of the eye by using a path length switching unit having multiple paths, and can be assembled to obtain a complete image. The upper deep sectional image 30 shows the cornea 32 and a part of the lens 33, while the lower deep sectional image 31 essentially shows the lens 33 and only a small sub-region of the cornea 32. As is apparent, the two deep sectional images 30, 33 have an overlapping region, in which common structures are present. It is advantageous if the deep sectional images that are recorded by way of the path length switching unit at different depths are predefined so that congruent overlapping regions are present. Because of the congruent structures present in the overlapping region, according to the invention information can be obtained about the relative positions of the individual deep sectional images. Based on this information, which is obtained and/or captured in particular by way of the evaluation unit, the deep sectional images 30, 31 are assembled to obtain a complete deep sectional image 34, as is shown on the right side. However, this overlapping region is not necessarily required because it is possible, by way of the design of the switching unit, to establish the relative positions of the measuring regions and thus, having knowledge of the geometry, a complete image can be computed.

Figure 9:
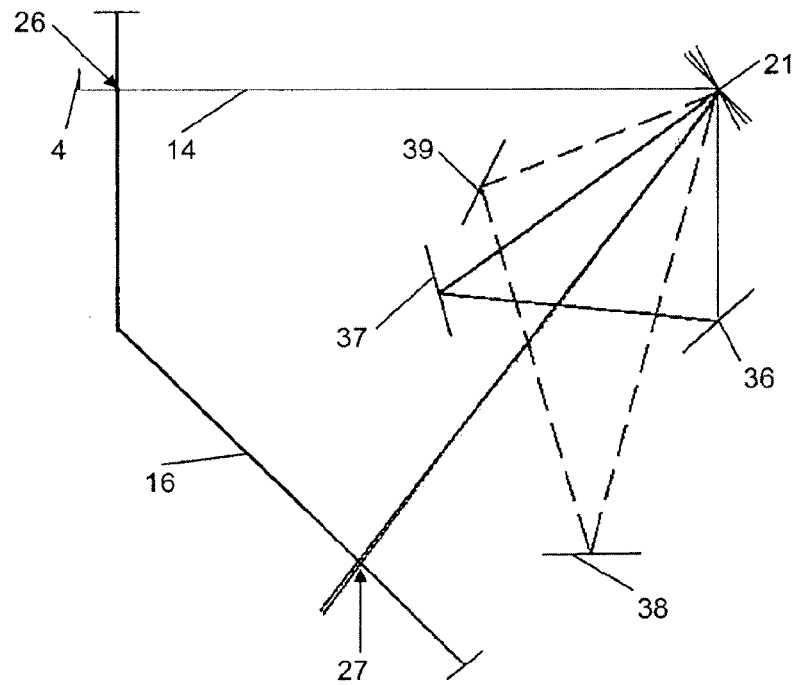
FIGS. 9, 10 show other special exemplary embodiments of the path length switching unit.
Figure 10:
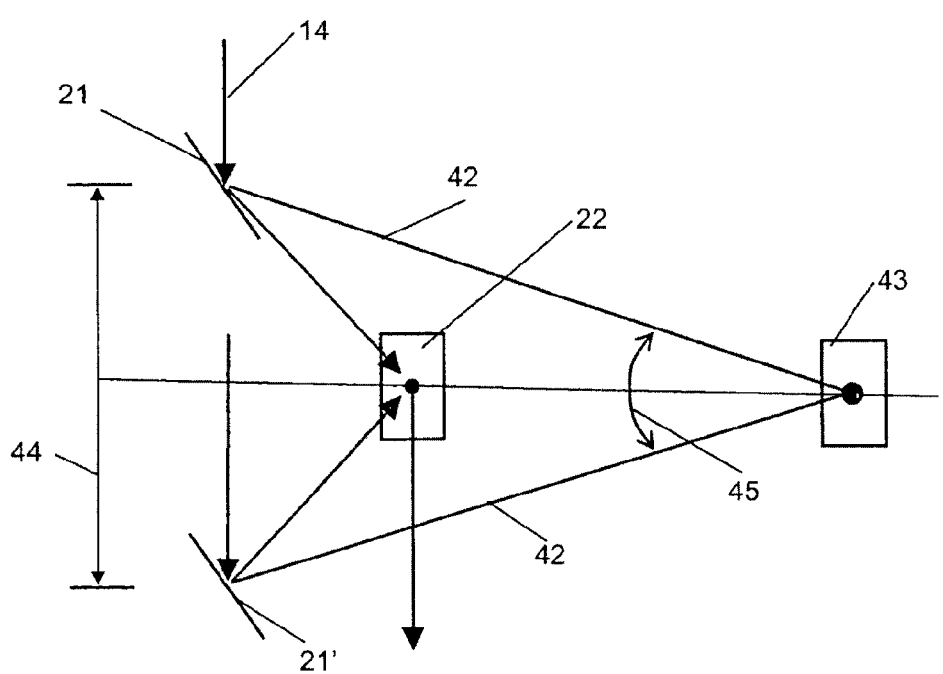

FIGS. 9 and 10 show examples of further possible embodiments of the path length switching unit.

FIG. 9 shows, by way of example, an arrangement comprising only one adjustable mirror 21, which can be rotated about an axis that is orthogonal to the drawing plane and on which the light beam 14 from the light source 4 impinges. Two mutually associated, preferably stationary, mirror pairs 38, 37 and 38, 39, which are disposed in the path length switching unit 16, are present. Depending on the angular position of the mirror 21, the incident light beam 14 is returned to the adjustable mirror 21 either by way of the mirror pair 36, 37 or the mirror pair 38, 39. The respective path lengths differ in accordance with the distances of the mirrors of the respective mirror pairs 36, 37 or 38, 39 from each other and from the adjustable mirror 21.

Of course, it is possible to provide more than two mirror pairs, or mirror groups in general, within the scope of the invention. The mirror groups may additionally comprise more than two mirrors.

In the exemplary embodiment of the path length switching unit shown in FIG. 10, the mirror 21 is connected via an arm 42 to a galvanometer 43, the pivot axis of which is orthogonal relative to the drawing plane. For the path length change 44, the mirror 21 is moved or pivoted by the angle 45 into the illustrated position 21' by way of the galvanometer 43. The additional mirror 22 can likewise be moved or pivoted by way of a galvanometer, which is not shown here. The rotational axis or pivot axis of the additional mirror 22 advantageously has a distance from the axis of the galvanometer 43, the distance being essentially half as large as the length of the arm 42. The mirror 22 is disposed so that the light beam reflected by the mirror 21 in the two shown positions essentially arrives at the center of the additional mirror 22, wherein the rotational or pivot axis of the associated galvanometer extends through the center. The design and operating principle of this embodiment, comprising the mirrors 21 and 22, including galvanometers, agrees with the device of U.S. Pat. No. 5,170,276, the disclosure of which is hereby expressly made the subject matter of the present patent application.

Figure 11:
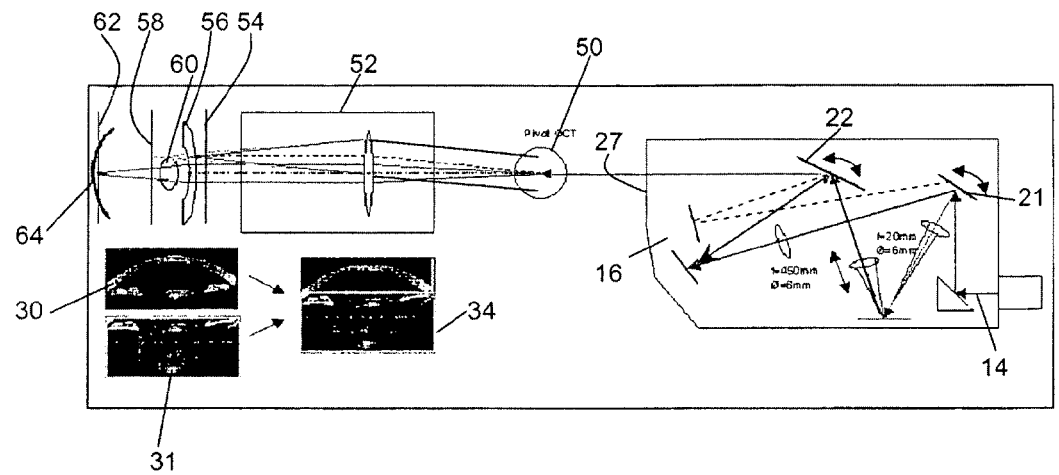
FIGS. 11, 12 show devices for analyzing an eye.
Figure 12:
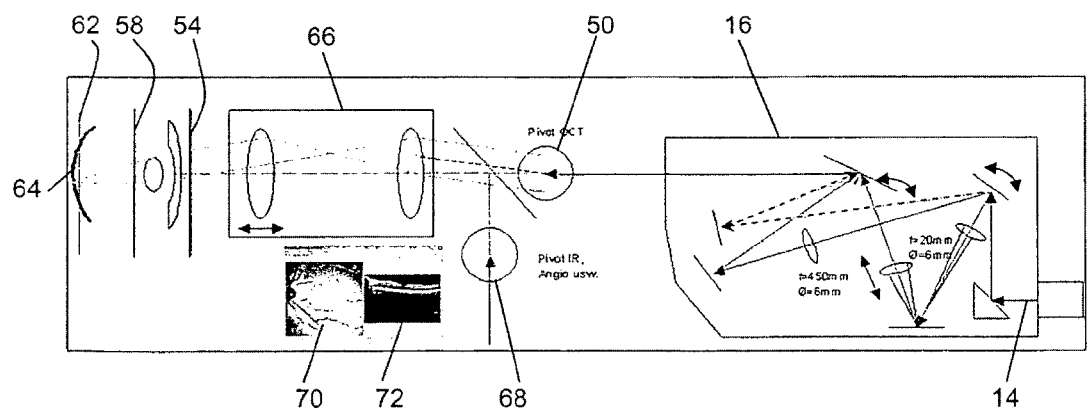

FIGS. 11 and 12 show two special devices for carrying out the method according to the invention, in particular for analyzing the eye. A device for representing and measuring all the structures of the human eye can be implemented with the aid of the path length switching unit 18 by using interchangeable lenses or modifying the imaging geometry by arranging optical components in the respective switched path.

A circle 50 denotes a pivot or a system axis of a device for optical coherence tomography (OCT). Optical coherence tomography allows two-dimensional sectional images and/or deep sectional images to be generated substantially perpendicular to the surface of the retina, and more particularly linearly based on depth A-scans. In addition, a replaceable lens 52 for biometrics and imaging of the anterior chamber is provided. Line 54 denotes the focus of the lens 52 in the region of the cornea 56, advantageously with a reference of 1 mm in front of the cornea at a distance of essentially sO +30 mm, In addition, line 58 denotes the focus in the lens 60, and more particularly with a reference of 1 mm behind the posterior lens 60, essentially at a distance sO +1 mm. Moreover, line 62 denotes the focus on the retina 64, and more particularly with reference in front of the retina sO. The device according FIG. 11 is additionally used to generate deep sectional images 30, 31 and assemble these to obtain a complete deep sectional image 34, as described based on FIG. 8.

Reference is made to the description of FIGS. 6 and 7 in relation to the path length switching unit 16.

The device shown in FIG, 12 includes a replaceable lens 66 for scanning the retina 64. A circle 68 denotes a pivot and/or axis for a system for generating a surface image 70 of the retina by angiography or as a reflectance image or autofluorescence image. Additionally, this device can be used to generate the deep sectional image 72, in particular by way of optical coherence tomography (OCT). The system and/or the device as well as the method are described in the patent application according to the publication U.S. Patent Application Publication No. US 2010/0053553 A1 and are described based on the drawings. The disclosure of this publication is hereby expressly incorporated by reference in the present patent application.

The device, in particular for analyzing the eye, can also be implemented without interchangeable lenses, by switching to different lenses using the path length switching unit according to the invention, comprising at least one adjustable mirror.

The invention claimed is:

1. A method for sequentially recording interferometric sectional images at different depths of a sample, comprising:
   providing an interferometer having an optical reference path and an optical sample path scanning a measuring region of the sample with a sample beam so as to generate a sectional image,
   wherein the sample beam is scanned at various lateral positions of the sample by a deflecting unit so as to generate said sectional image,
   wherein path length of either or both the sample beam and the reference beam is changed by a path length switching unit having a plurality of first mirrors having an adjustable orientation and plurality of second mirrors having a fixed orientation and the sample beam at all path length configurations impinges upon each mirror of said plurality of first minors and at least one mirror of said plurality of second mirrors, and sectional images are generated at least at two different depths of the sample by scanning with the sample beam a different respective measuring region of the sample at each said different depth, and
   wherein the change of the path length in the switching unit takes place by deflection of the beam paths to different geometric paths.

2. The method according to claim 1, further comprising providing the switching unit with at least one mirror which is either or both movably and rotatably disposed and adjusting at least one said mirror to two different angular positions.

3. The method according to claim 1, further comprising computing the sectional image by evaluating interferometric signals of the interferometer which result from superimposition of the sample beams and reference beams at either or both different lateral positions and different depth positions on the sample.

4. The method according to claim 2, further comprising setting either or both the sample beam and the reference beam by way of at least one said mirror of the path length switching unit so that the sample beam and the reference beam enter and exit the path length switching unit at respective different positions independently of the position of the at least one said mirror.

5. The method according to claim 2, wherein the movement or rotation of at least one said mirror is carried out by way of a motor associated therewith.

6. The method according to claim 1, further comprising providing an optical unit and focusing the sample beam to a predetermined depth of the sample by way of the optical unit, the focus being suited to a depth that is predefined by way of the path length switching unit.

7. The method according to claim 1, further comprising assembling a complete sectional image from at least two said sectional images.

8. A complete sectional image generated by the method of claim 1, wherein the complete sectional image is generated with use of coinciding reference signals of the respective said sectional images.

9. An apparatus for carrying out method of claim 1, comprising the interferometer having the optical reference path and the optical sample path, the interferometer being configured to scan respective said measuring regions of the sample by way of the sample beam, the apparatus further comprising the path length switching unit disposed in either or both the optical reference path and the optical sample path, wherein the unit can be used to change or predetermine the length of either or both the optical reference path and the optical sample path so that the respective measuring regions in the sample can be predetermined at least at two respectively different measuring depths.

10. The apparatus according to claim 9, wherein the path length switching unit comprises the at least one mirror which is either or both movable and rotatable and which can be set to at least two different positions by way of a motor.

11. The apparatus according to claim 2, wherein the path length switching unit comprises at least one further mirror which is stationary.

12. The apparatus according to claim 9, further comprising, in at least one of the optical paths, a respective optical unit by way of which focus position, dispersion or imaging geometry for the respective measuring region can be predetermined.

13. The method according to claim 1, wherein the sample is an eye.

14. The method according to claim 7, further comprising providing an evaluation unit and assembling the complete sectional image by way of the evaluation unit.

15. The method according to claim 1, further comprising capturing the relative position of the scanned regions.

16. The method according to claim 1, further comprising capturing the sectional images as respective sectional sub-images.

17. The complete sectional image according to claim 8, wherein the complete sectional image is generated with use by an evaluation unit of the coinciding reference signals of the respective said sectional images.

18. A complete sectional image generated by the method of claim 1, wherein the complete sectional image is generated with use of reference signals of the respective said sectional images generated based on identical structures.

19. The complete sectional image according to claim 18, wherein the identical structures are in an overlapping region of the respective sectional images.

20. The apparatus according to claim 10, wherein the motor comprises a galvanometer.

21. The apparatus according to claim 11, wherein the at least one said stationary mirror is disposed so that, in cooperation with the at least one said mirror which is either or both movable and rotatable, the sample beam and the reference beam enter and exit the path length switching unit at respective different positions independently of the position of each said at least one mirror which is either or both movable and rotatable.

22. The method according to claim 1, wherein the sample beam scanning said measuring region encompasses in order from a beam splitter of the interferometer: the switching unit, the deflection unit, and an optical unit.

* * * * *